(12) United States Patent
Fujiyoshi et al.

(10) Patent No.: US 10,068,943 B2
(45) Date of Patent: Sep. 4, 2018

(54) RADIATION IMAGING APPARATUS AND RADIATION IMAGING SYSTEM

(71) Applicant: CANON KABUSHIKI KAISHA, Tokyo (JP)

(72) Inventors: Kentaro Fujiyoshi, Tokyo (JP); Minoru Watanabe, Yokohama (JP); Keigo Yokoyama, Kawasaki (JP); Masato Ofuji, Takasaki (JP); Jun Kawanabe, Kawasaki (JP); Hiroshi Wayama, Kawasaki (JP); Kazuya Furumoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/543,415

(22) PCT Filed: Mar. 17, 2016

(86) PCT No.: PCT/JP2016/001562
§ 371 (c)(1),
(2) Date: Jul. 13, 2017

(87) PCT Pub. No.: WO2016/152120
PCT Pub. Date: Sep. 29, 2016

(65) Prior Publication Data
US 2018/0006080 A1 Jan. 4, 2018

(30) Foreign Application Priority Data
Mar. 20, 2015 (JP) .................. 2015-058128

(51) Int. Cl.
*H01L 27/146* (2006.01)
*A61B 6/00* (2006.01)
(Continued)

(52) U.S. Cl.
CPC ...... *H01L 27/14658* (2013.01); *A61B 6/4233* (2013.01); *H01L 27/14609* (2013.01);
(Continued)

(58) Field of Classification Search
CPC ......... H01L 27/14658; H01L 27/14609; A61B 6/4233; H04N 5/37452; H04N 5/378; H04N 5/37455
See application file for complete search history.

(56) References Cited

U.S. PATENT DOCUMENTS

| 6,243,441 B1 | 6/2001 | Zur |
| 6,838,673 B2 | 1/2005 | Morishita |

(Continued)

FOREIGN PATENT DOCUMENTS

| JP | 2001-116846 A | 4/2001 |
| JP | 2002-139571 A | 5/2002 |

(Continued)

*Primary Examiner* — Christine S Kim
(74) *Attorney, Agent, or Firm* — Fitzpatrick, Cella, Harper & Scinto

(57) ABSTRACT

Provided is a radiation imaging apparatus, including: a plurality of pixels configured to output image signals corresponding to radiation; an image signal line configured to output the image signals; and a detection signal line configured to output a detection signal for detection of irradiation of the radiation, in which at least one of the plurality of pixels includes: a conversion element configured to convert the radiation into charge; a first switch configured to output the image signal corresponding to the charge via the image signal line; a storage capacitor including a first electrode and a second electrode, in which the first electrode is electrically connected to the conversion element to store the charge; and a second switch configured to electrically connect the second electrode and the detection signal line.

12 Claims, 13 Drawing Sheets

(51) Int. Cl.
*H04N 5/378* (2011.01)
*H04N 5/3745* (2011.01)

(52) U.S. Cl.
CPC ......... *H04N 5/378* (2013.01); *H04N 5/37452* (2013.01); *H04N 5/37455* (2013.01)

(56) References Cited

U.S. PATENT DOCUMENTS

| | | |
|---|---|---|
| 7,435,968 B2 | 10/2008 | Watanabe et al. |
| 7,535,506 B2 | 5/2009 | Nomura et al. |
| 7,557,355 B2 | 7/2009 | Mochizuki et al. |
| 7,645,976 B2 | 1/2010 | Watanabe et al. |
| 7,812,313 B2 | 10/2010 | Mochizuki et al. |
| 7,812,317 B2 | 10/2010 | Watanabe et al. |
| 7,858,947 B2 | 12/2010 | Mochizuki et al. |
| 8,154,641 B2 | 4/2012 | Nomura et al. |
| 8,368,027 B2 | 2/2013 | Ishii et al. |
| 8,680,472 B2 | 3/2014 | Mochizuki et al. |
| 9,521,347 B2 | 12/2016 | Kawanabe et al. |
| 9,726,767 B2 | 8/2017 | Kawanabe et al. |
| 2002/0066861 A1 | 6/2002 | Morishita |
| 2004/0101100 A1* | 5/2004 | Morii ............... H01L 27/14658 378/98.7 |
| 2007/0211858 A1* | 9/2007 | Franklin ........... H01L 27/14658 378/97 |
| 2009/0321643 A1* | 12/2009 | Rutten ............. H01L 27/14658 250/338.4 |
| 2013/0208860 A1* | 8/2013 | Sugizaki ............... G01T 1/2928 378/62 |
| 2013/0223592 A1* | 8/2013 | Sato ....................... A61B 6/542 378/62 |
| 2015/0078528 A1* | 3/2015 | Okada ..................... G01T 1/026 378/97 |
| 2015/0182182 A1* | 7/2015 | Tajima ..................... H04N 5/32 378/189 |
| 2015/0316661 A1 | 11/2015 | Fujiyoshi et al. |
| 2017/0229502 A1* | 8/2017 | Liu .................... H01L 27/14609 |
| 2017/0234994 A1* | 8/2017 | Nishihara ............. G01T 1/2018 250/361 R |
| 2017/0264838 A1* | 9/2017 | Maes .................... H04N 5/3559 |

FOREIGN PATENT DOCUMENTS

| | | |
|---|---|---|
| JP | 2009-188650 A | 8/2009 |
| JP | 2012-95967 A | 5/2012 |
| JP | 2013-135390 A | 7/2013 |

* cited by examiner

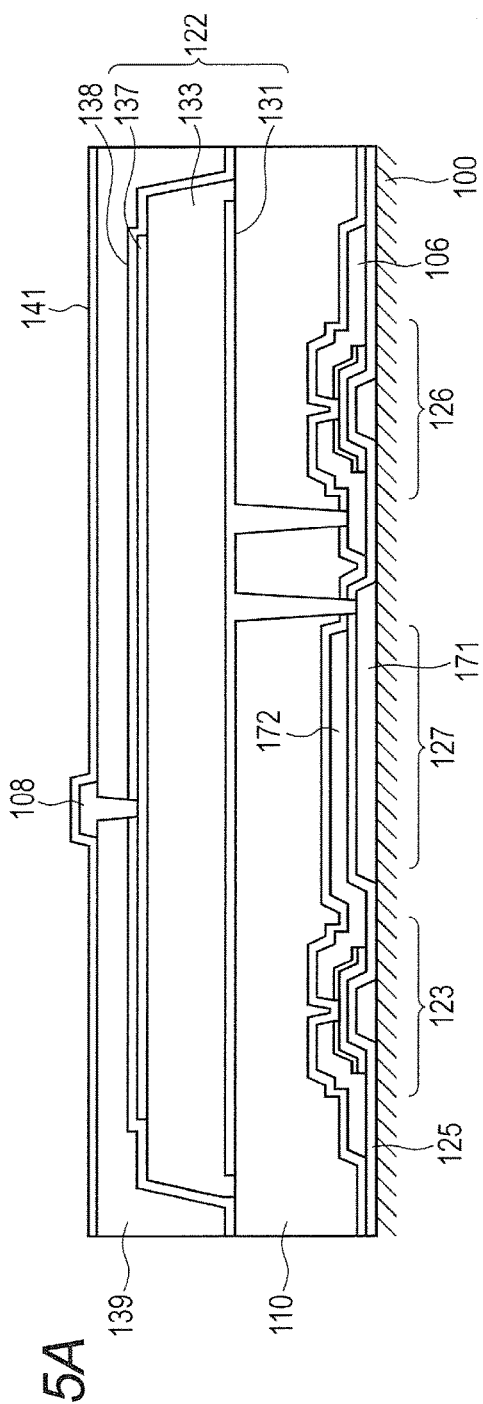
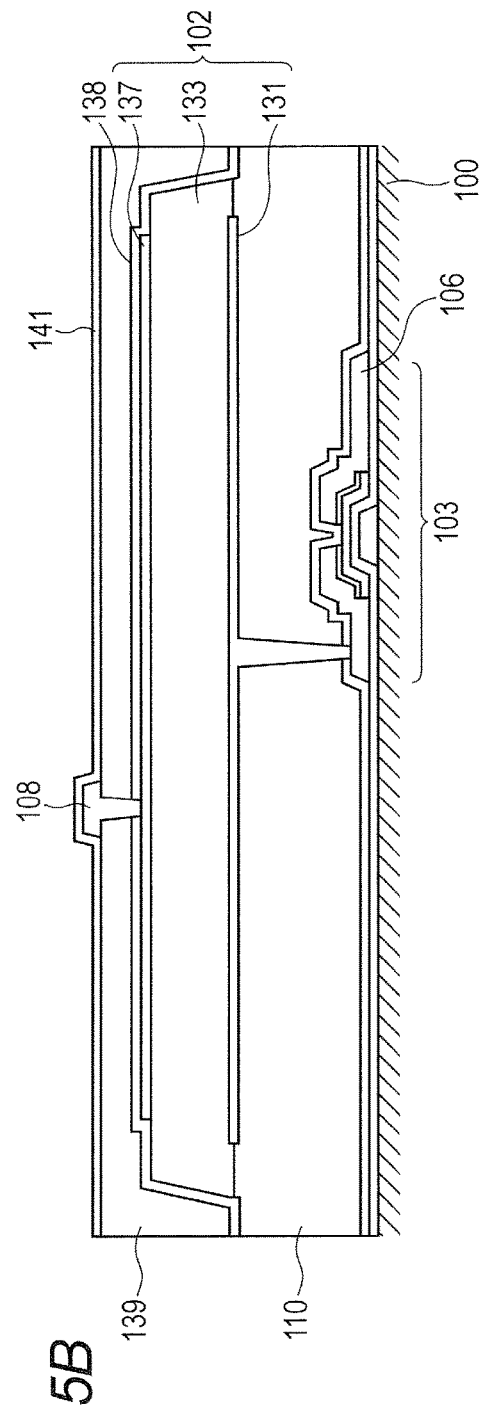

RADIATION IMAGING APPARATUS AND RADIATION IMAGING SYSTEM

TECHNICAL FIELD

The present invention relates to a radiation imaging apparatus and a radiation imaging system.

BACKGROUND ART

As a radiographic apparatus for use in medical diagnostic imaging or nondestructive inspection with radiation such as an X-ray, a radiation imaging apparatus in which pixels each formed by combining a switch such as a thin-film transistor (TFT) and a conversion element such as a photoelectric conversion element are arranged has been put into practical use. The switch is arranged between the conversion element and a column signal line, and the switch is put into a conductive state to read out a signal from the conversion element via the column signal line. In recent years, increasing functionality of the radiation imaging apparatus has been considered. As one function, including a function of monitoring radiation irradiation has been considered. This function enables detection of a timing at which the radiation irradiation from a radiation source is started, detection of a timing to stop the radiation irradiation, and detection of an irradiation amount or an integrated irradiation amount of the radiation, for example.

In Patent Literature 1, there is disclosed a radiation detector configured to detect an irradiation amount of radiation to detect a timing to stop radiation irradiation, and to acquire a radiation image. The radiation detector according to Patent Literature 1 includes a photoelectric conversion element, a line for reading out radiation image data, a line for reading out radiation irradiation amount data, a switch element, and a storage capacitor. The line for reading out the radiation image data is connected to the photoelectric conversion element via the switch element, and the storage capacitor is arranged between the line for reading out the radiation irradiation amount data and the photoelectric conversion element.

According to the structure described in Patent Literature 1, in a case where the irradiation amount of the radiation is detected, the radiation irradiation amount data is read out via the storage capacitor, with the result that an amount of charge generated by the radiation is stored, and the radiation image data is not attenuated. Therefore, also in a pixel for detecting a radiation irradiation amount, image data may be obtained without being attenuated.

CITATION LIST

Patent Literature

PTL 1: Japanese Patent Application Laid-Open No. 2001-116846

SUMMARY OF INVENTION

Technical Problem

In the radiation detector according to Patent Literature 1, in order to individually detect the radiation irradiation on an arbitrary detection region, the same number of dedicated signal lines as the number of detection regions are required, which restricts the layout. Moreover, the radiation irradiation on a detection region at an arbitrary position cannot be detected at an arbitrary timing.

Solution to Problem

The present invention provides a technology capable of detecting radiation at an arbitrary position at an arbitrary timing without restricting the layout, and of reading out pixel signals without attenuation even when an amount of radiation is monitored.

According to one embodiment of the present invention, there is provided a radiation imaging apparatus, including: a plurality of pixels configured to output image signals corresponding to radiation; an image signal line configured to output the image signals; and a detection signal line configured to output a detection signal for detection of irradiation of the radiation, in which at least one of the plurality of pixels includes: a conversion element configured to convert the radiation into charge; a first switch configured to output the image signal corresponding to the charge via the image signal line; a storage capacitor including a first electrode and a second electrode, in which the first electrode is electrically connected to the conversion element to store the charge; and a second switch configured to electrically connect the second electrode and the detection signal line.

Further features of the present invention will become apparent from the following description of exemplary embodiments with reference to the attached drawings.

BRIEF DESCRIPTION OF DRAWINGS

FIG. 5A is a cross-sectional view taken along the line A-A in FIG. 4.

FIG. 5B is a cross-sectional view taken along the line B-B in FIG. 4.

DESCRIPTION OF EMBODIMENTS

First Embodiment

Preferred embodiments of the present invention will now be described in detail in accordance with the accompanying drawings.

Figure 1:
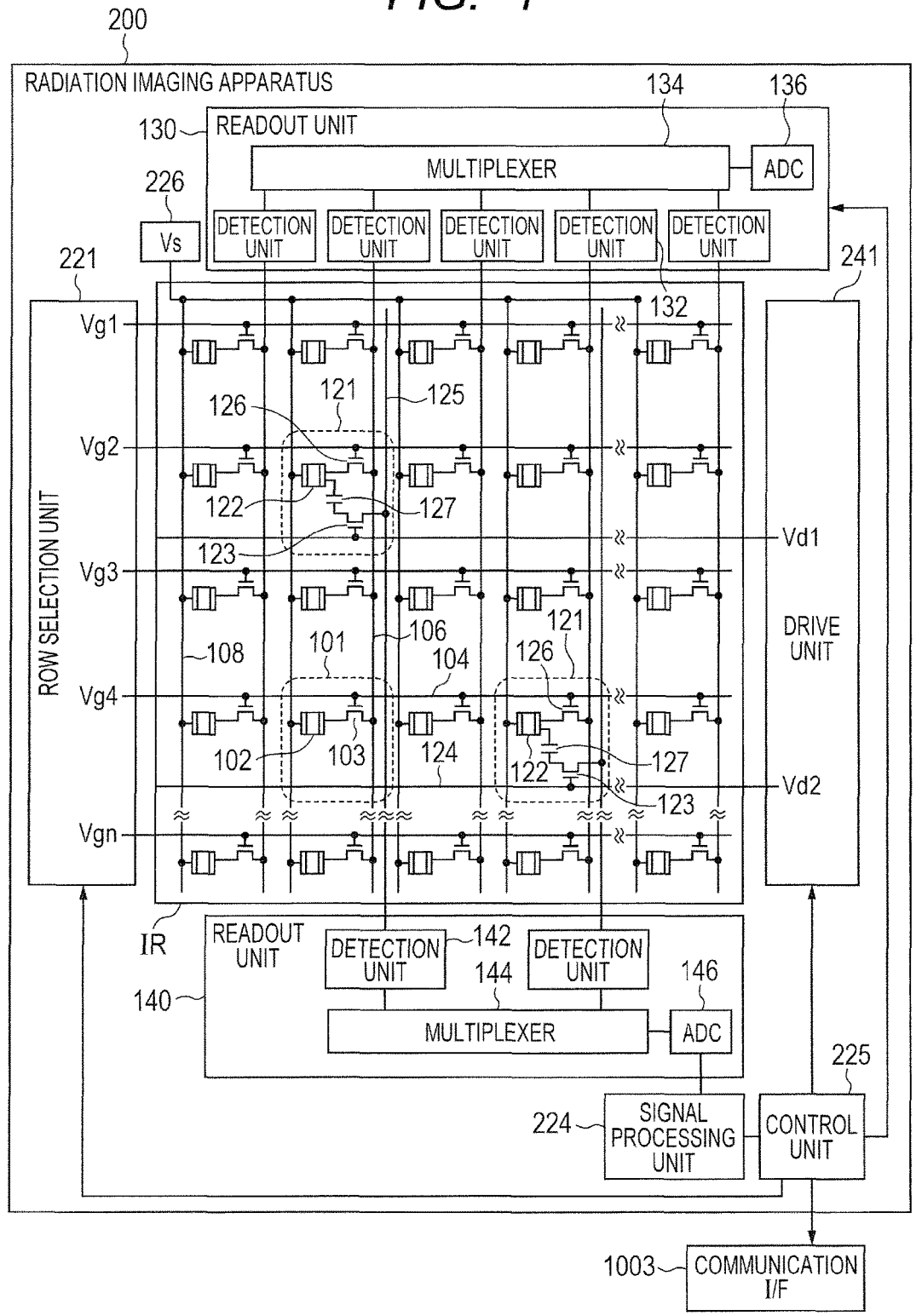
FIG. 1 is a diagram for illustrating a configuration example of a radiation imaging apparatus.

In FIG. 1, a configuration example of a radiation imaging apparatus 200 according to a first embodiment of the present invention is illustrated. The radiation imaging apparatus 200 includes an imaging region IR, readout units 130 and 140, a row selection unit 221, a drive unit 241, a signal processing unit 224, a control unit 225, and a power supply circuit 226. The imaging region IR includes a plurality of pixels 101 and 121 arranged in matrix. The plurality of pixels include a plurality of imaging pixels (second pixels) 101 configured to acquire a radiation image, and detection pixels (first pixels) 121 configured to monitor radiation irradiation. Each of the imaging pixels 101 includes a first conversion element 102 configured to convert radiation into an electrical signal (charge), and a first switch 103. The first switch 103 is connected between a column signal line (image signal line) 106 and the first conversion element 102. Each of the detection pixels 121 includes a second conversion element 122 configured to convert the radiation into an electrical signal (charge), a second switch 123, a storage capacitor 127, and a third switch 126. The second switch 123 is connected between a detection signal line 125 and the storage capacitor 127. The storage capacitor 127 is connected between the second switch 123 and the second conversion element 122. The third switch 126 is connected between the column signal line 106 and the second conversion element 122. The imaging pixels 101 are arranged in all columns. The detection pixels 121 are arranged in some columns.

Each of the first conversion element 102 and the second conversion element 122 includes a scintillator configured to convert the radiation into light, and a photoelectric conversion element configured to convert the light into an electrical signal. The scintillator is formed into a sheet shape to cover the imaging region IR, and is shared by the plurality of pixels 101 and 121. Note that, each of the first conversion element 102 and the second conversion element 122 may be a conversion element configured to directly convert the radiation into the light. Each of the first switch 103, the second switch 123, and the third switch 126 includes a thin-film transistor (TFT) having an active region formed of a semiconductor such as amorphous silicon or polysilicon (preferably, polysilicon), for example.

The radiation imaging apparatus 200 includes a plurality of column signal lines 106 and a plurality of drive lines 104. The plurality of column signal lines 106 are provided for respective columns, and each column signal line 106 is connected in common to the pixels 101 and 121 in each column. The plurality of drive lines 104 are provided for respective rows, and each drive line 104 is connected in common to the pixels 101 and 121 in each row. The plurality of drive lines 104 are driven by the row selection unit 221.

A first electrode of the first conversion element 102 is connected to a first main electrode of the first switch 103, and a second electrode of the first conversion element 102 is connected to a bias line 108. A plurality of bias lines 108 are provided for respective columns, and each bias line 108 is connected in common to second electrodes of the conversion elements 102 and 122 in each column. The bias line 108 receives a bias voltage Vs from the power supply circuit 226. Second main electrodes of the first switches 103 in each column are connected to the column signal line 106 in each column. Control electrodes of the first switches 103 in each row are connected to the drive line 104 in each row.

The plurality of column signal lines 106 are connected to a second readout unit 130. The second readout unit 130 includes a plurality of detection units 132, a multiplexer 134, and an analog-to-digital converter (hereinafter referred to as "AD converter") 136, and is configured to read out signals from the column signal lines 106. The plurality of detection units 132 are provided for respective columns, and each detection unit 132 is connected to the column signal line 106 in each column. The column signal line 106 in each column is connected to the detection unit 132 in each column. The detection unit 132 includes an amplifier, for example. The multiplexer 134 is configured to select the plurality of detection units 132 in predetermined order, and supply a signal from the selected detection unit 132 to the AD converter 136. The AD converter 136 is configured to subject the supplied signal to analog-to-digital conversion and outputs the converted signal.

A first electrode of the second conversion element 122 is connected to a second electrode of the storage capacitor 127 and a first main electrode of the third switch 126. A first electrode of the storage capacitor 127 is connected to a first main electrode of the second switch 123. A second main electrode of the second switch 123 is connected to the detection signal line 125. A second main electrode of the third switch 126 is connected to the column signal line 106. A second electrode of the second conversion element 122 is connected to the bias line 108. A control electrode of the second switch 123 is connected to a drive line 124. A control electrode of the third switch 126 is connected to the drive line 104. The radiation imaging apparatus 200 includes a plurality of detection signal lines 125. To each of the plurality of detection signal lines 125, one or a plurality of detection pixels 121 may be connected. The drive line 124 is driven by the drive unit 241. To each of a plurality of drive lines 124, one or a plurality of detection pixels 121 may be connected.

The detection signal line 125 is connected to a first readout unit 140. The first readout unit 140 includes a plurality of detection units 142, a multiplexer 144, and an AD converter 146, and is configured to read out signals from the detection signal line 125. The plurality of detection signal lines 125 are connected to the detection units 142. One of the detection signal lines correspond to one of the detection units 142. The detection unit 142 includes an amplifier, for example. The multiplexer 144 is configured to select the plurality of detection units 142 in predetermined order, and supply a signal from the selected detection unit 142 to the AD converter 146. The AD converter 146 is configured to subject the supplied signal to analog-to-digital conversion and outputs the converted signal.

The output signal of the AD converter 146 is supplied to the signal processing unit 224. The signal processing unit 224 is configured to output information indicating the radiation irradiation on the radiation imaging apparatus 200 based on the output signal of the AD converter 146. More specifically, the signal processing unit 224 is configured to detect the radiation irradiation on the radiation imaging apparatus 200, and compute an irradiation amount and/or an integrated irradiation amount of the radiation, for example. The control unit 225 is configured to control the row selection unit 221, the drive unit 241, and the readout unit 130 based on the information from the signal processing unit 224. The control unit 225 is configured to control start and termination of exposure (storage of the charge corresponding to the irradiated radiation by the imaging pixels 101) based on the information from the signal processing unit 224, for example. The control unit 225 is also configured to control a communication interface 1003.

Figure 2:
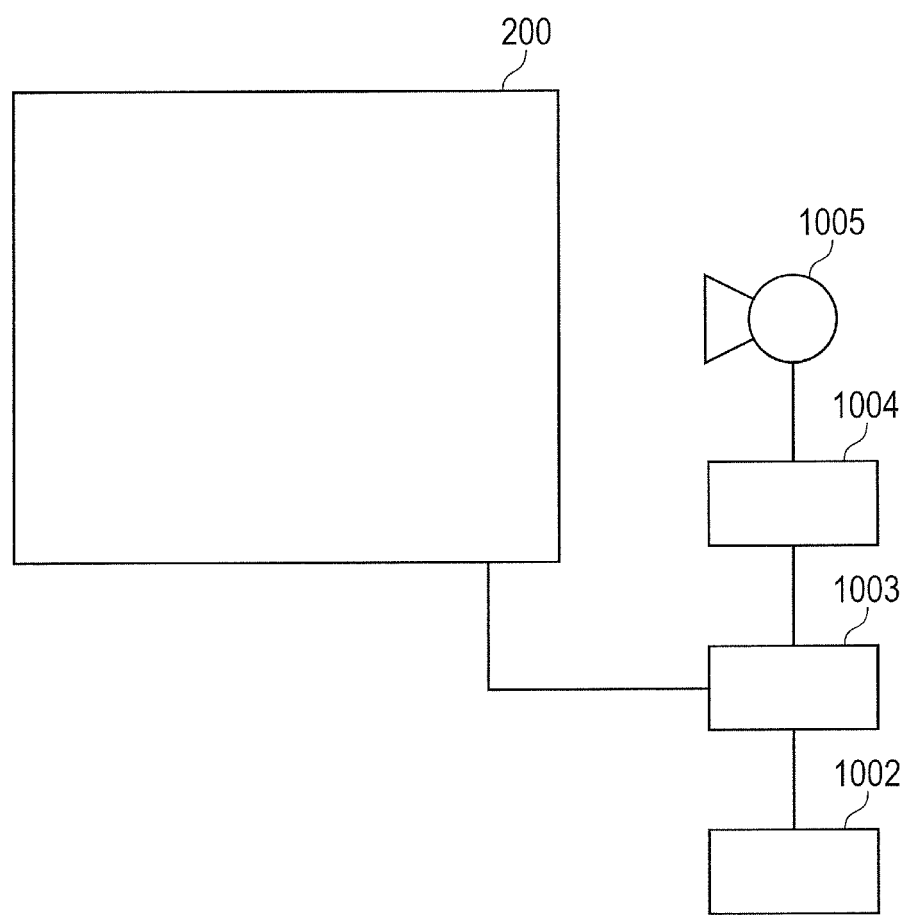
FIG. 2 is a diagram for illustrating a configuration example of a radiation imaging system.

FIG. 2 is a diagram for illustrating a configuration example of a radiation imaging system including the radiation imaging apparatus 200. The radiation imaging system includes, in addition to the radiation imaging apparatus 200 of FIG. 1, a controller 1002, the communication interface 1003, a radiation source interface 1004, and a radiation source 1005. The controller 1002 receives as inputs a dose A, irradiation time B (ms), a tube current C (mA), a tube voltage D (kV), a radiation detection region (region of interest: ROI), which is a region to be monitored for the radiation, and the like. The controller 1002 is configured to output input information to the radiation imaging apparatus 200 via the communication interface 1003. When an exposure switch attached to the radiation source 1005 is operated, the radiation is irradiated from the radiation source 1005. The radiation imaging apparatus 200 is configured to use the detection pixels 121 arranged in the radiation detection region (ROI) to perform a detection operation for detecting the radiation irradiation, and to detect a timing at which the radiation irradiation is started, for example. Next, when an integrated value of signals read out from the detection pixels 121 arranged in the radiation detection region (ROI) has reached a dose A1, the control unit 225 is configured to output an exposure stop signal to the radiation source interface 1004 via the interface 1003, for example. In response thereto, the radiation source interface 1004 causes the radiation source 1005 to stop the radiation irradiation. Here, the dose A1 is determined by the control unit 225 based on the dose A, a radiation irradiation intensity, a communication delay between each pair of units, a processing delay, and the like. In a case where irradiation time of the radiation has reached the irradiation time B, the radiation source 1005 stops the radiation irradiation regardless of whether or not the exposure stop signal has been output.

Figure 3:
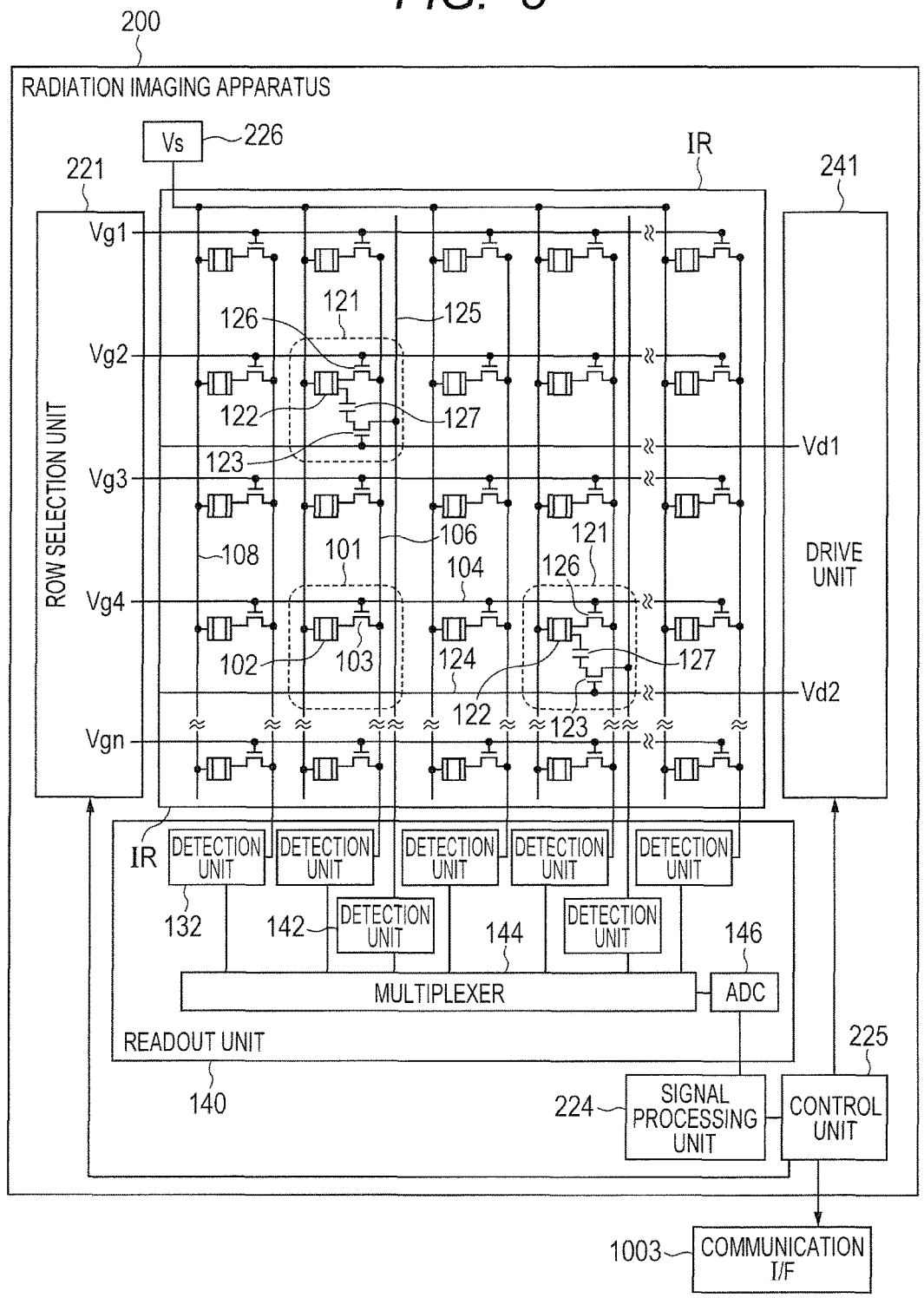
FIG. 3 is a diagram for illustrating another configuration example of the radiation imaging apparatus.

In the configuration example of FIG. 1, the signals from the column signal lines 106, which are output from the imaging pixels 101, are read out by the readout unit 130, and the signals from the detection signal line 125, which are output from the detection pixels 121, are read out by the readout unit 140, but the present invention is not limited thereto. As illustrated in FIG. 3, the signals from the column signal lines 106, which are output from the imaging pixels 101, and the signals from the detection signal line 125, which are output from the detection pixels 121, may be read out by a common readout unit 140. The readout unit 140 includes the plurality of detection units 132, the plurality of detection units 142, the multiplexer 144, and the AD converter 146. The multiplexer 144 has functions of the multiplexers 134 and 144 in FIG. 1. The AD converter 146 has functions of the AD converters 136 and 146 in FIG. 1.

Figure 4:
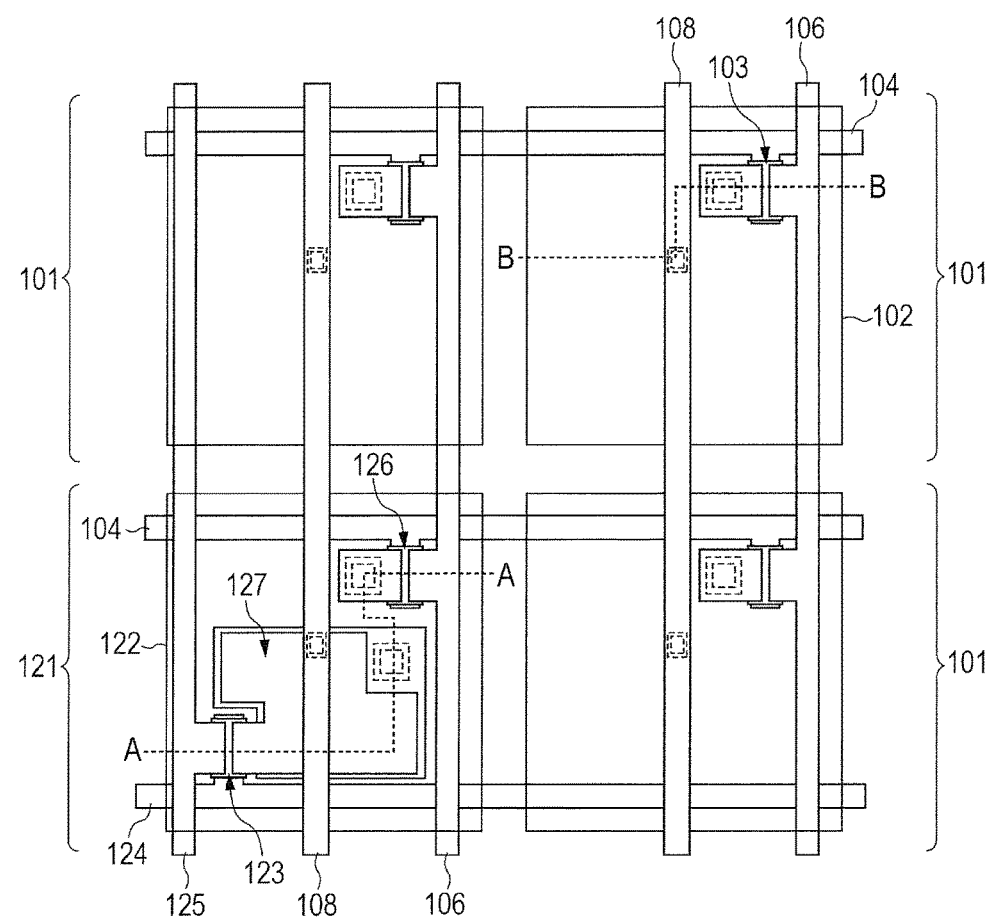
FIG. 4 is a plan view for illustrating a configuration example of imaging pixels and detection pixels.

FIG. 4 is a plan view for illustrating a configuration example of the imaging pixels 101 and the detection pixel 121. This plan view is an orthographic drawing of the radiation imaging apparatus 200 on a plane parallel to the imaging region IR. FIG. 5A is a cross-sectional view taken along the line A-A in FIG. 4, and FIG. 5B is a cross-sectional view taken along the line B-B in FIG. 4.

As illustrated in FIG. 4 and FIG. 5A, the detection pixel 121 includes the second conversion element 122, the second switch 123, the third switch 126, and the storage capacitor 127. In this example, the second conversion element 122 is configured to convert the light, which has been converted from the radiation by the scintillator, into the charge and store the charge. Note that, the second conversion element 122 may be configured to directly convert the radiation into the charge. The second switch 123 includes a thin-film transistor (TFT) configured to output the electrical signal corresponding to the charge stored in the second conversion element 122. The second conversion element 122 includes a PIN photodiode 133, for example. The second conversion element 122 is connected to a second electrode 172 of the storage capacitor 127. A first electrode 171 of the storage capacitor 127 is connected to the detection signal line 125 via the second switch 123. The second conversion element 122 is also connected to the signal line 106 via the third switch 126. The second conversion element 122 is arranged above the second switch 123, the third switch 126, and the storage capacitor 127, which are arranged on an insulating support substrate 100 such as a glass substrate, with interposition of a first interlayer insulating layer 110. The second conversion element 122 includes a first electrode 131, the PIN photodiode 133, and a second electrode 137, for example.

Above the second conversion element 122, a protective film 138, a second interlayer insulating layer 139, the bias line 108, and a protective film 141 are arranged in the stated order. On the protective film 141, a planarization film and the scintillator are arranged. The second electrode 137 is connected to the bias line 108 via a contact hole. The second electrode 137 uses optically transparent ITO and is configured to be able to transmit the light converted from the radiation by the scintillator.

As illustrated in FIG. 4 and FIG. 5B, the imaging pixel 101 includes the first conversion element 102 and the first switch 103. As with the second conversion element 122, the first conversion element 102 is configured to convert the light, which has been converted from the radiation by the scintillator, into the charge and store the charge. Note that, the first conversion element 102 may be configured to directly convert the radiation into the charge. The first switch 103 includes a thin-film transistor (TFT) configured to output the electrical signal corresponding to the charge stored in the first conversion element 102. The first conversion element 102 includes the PIN photodiode 133, for example. The first conversion element 102 is connected to the column signal line 106 via the first switch 103. The first conversion element 102 is arranged above the first switch 103, which is arranged on the insulating support substrate 100 such as the glass substrate, with interposition of the first interlayer insulating layer 110. The first conversion element 102 includes the first electrode 131, the PIN photodiode 133, and the second electrode 137, for example. Each of the first conversion element 102 and the second conversion element 122 may be formed of a metal-insulator-semiconductor (MIS) sensor, for example.

In the example of FIG. 5A, in the storage capacitor 127, not only capacitance between the first electrode 171 and the second electrode 172, but also capacitance generated by the first interlayer insulating layer 110 between the second electrode 172 and the first electrode 131 of the second conversion element 122 may contribute as the storage capacitor. Moreover, the form of the storage capacitor 127 in FIG. 5A is merely an example, and the example in which the storage capacitor 127 is formed under the first interlayer insulating layer 110 has been described, but the present invention is not limited thereto. A configuration in which the first interlayer insulating layer 110 is formed as an insulating layer formed of two layers, a conductive layer is formed between the two layers, and the storage capacitor is formed with the conductive layer arranged in a lower portion of the first interlayer insulating layer 110 may be adopted.

Figure 6:
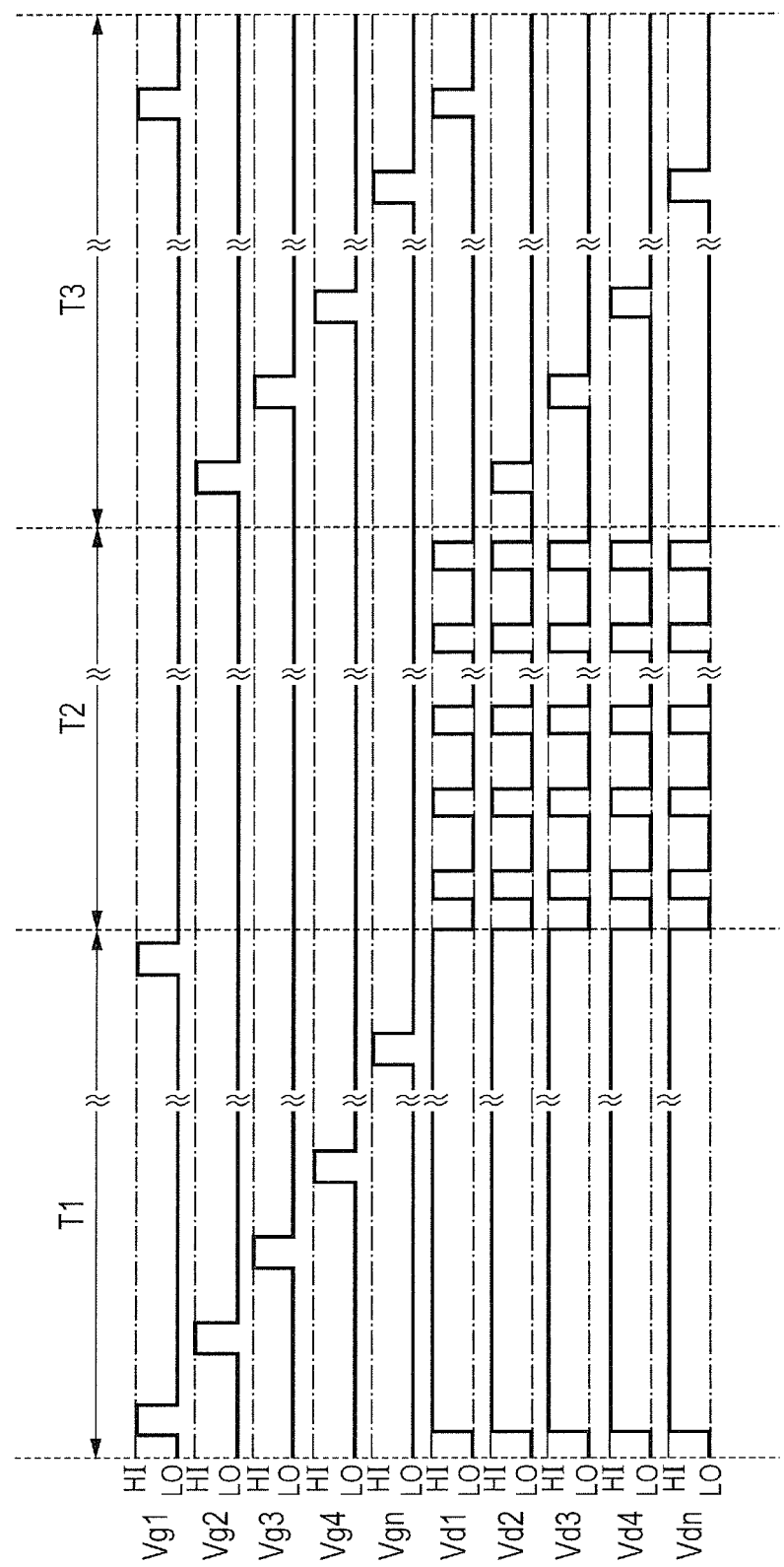
FIG. 6 is a timing chart for illustrating operations of the radiation imaging apparatus.

FIG. 6 is a timing chart for illustrating an example of a method of driving the radiation imaging apparatus 200 according to this embodiment. In the following description, signals applied to the drive lines 104 for driving the first switches 103 of the imaging pixels 101 and the third switches 126 of the detection pixels 121 are denoted as Vg1 to Vgn. Moreover, signals applied to the drive lines 124 for driving the second switches 123 of the detection pixels 121 are denoted as Vd1 to Vdn (see FIG. 7). Each of the first switches 103, the second switches 123, and the third switches 126 is in a conductive state when the signal supplied to a gate thereof is at a high level, and is in a non-conductive state when the signal supplied to the gate thereof is at a low level.

Period T1 is a period to wait for the start of the radiation irradiation. More specifically, Period T1 is a period from when the radiation imaging apparatus 200 is powered on to enter a state capable of capturing the radiation image to when the exposure switch of the radiation source 1005 is operated and the radiation imaging apparatus 200 detects the radiation irradiation.

In Period T1, the signals Vd1 to Vdn are fixed to the high level, and the second switches 123 of the detection pixels 121 are fixed to the conductive state. When the radiation is irradiated, the second conversion element 122 converts the radiation into the charge, and the charge is stored in each of the second conversion element 122 and the storage capacitor 127 depending on a capacity ratio between the second conversion element 122 and the storage capacitor 127. Depending on an amount of charge stored in the storage capacitor 127, the detection signal line 125 transmits a signal to the readout unit 140. The readout unit 140 is configured to amplify the signal by the detection unit 142, subject the signal to the analog-to-digital conversion by the AD converter, and output the converted signal to the signal processing unit 224. The signal processing unit 224 is configured to detect the start of the radiation irradiation based on the output signal of the AD converter 146. When the start of the radiation irradiation is detected, the operation transitions to Period T2. In Period T1, in order to remove a dark current generated in the first conversion element 102, each of the first conversion elements 102 may be periodically reset to a constant potential. In this example, the signals Vg1 to Vgn from the respective drive lines 104 are sequentially set to the high level, the first switches 103 in each column are sequentially set to the conductive state, and the first conversion elements 102 in each column are sequentially electrically connected to the column signal line 106 that is fixed to a constant voltage. In this manner, charge caused by the dark current is prevented from being stored in the first conversion element 102 for a long period of time. The length of Period T1 is significantly different depending on photographing methods and conditions and the like, and is several seconds to several minutes, for example.

Period T2 is a period during which the radiation is irradiated. As an example, Period T2 is a period from when the radiation imaging apparatus 200 detects the start of the radiation irradiation to when an amount of exposure to the radiation reaches an optimal dose. Period T2 may also be regarded as a period during which the irradiation amount of the radiation is monitored. In Period T2, the signals Vd1 to Vdn are intermittently set to the high level, and the second switches 123 of the detection pixels 121 intermittently enter the conductive state. The second conversion element 122 is configured to convert the radiation into the charge. The detection signal line 125 is configured to transmit the signals to the readout unit 140 depending on the amount of charge stored in the storage capacitor 127. The signal processing unit 224 is configured to detect a dose of the radiation based on an output signal of the readout unit 140. In Period T2, the signals Vg1 to Vgn applied to the respective drive lines 104 are set to the low level, and the first switches 103 are fixed to the non-conductive state. In this manner, the first conversion element 102 of the imaging pixel 101 converts the radiation into the charge, and stores the converted charge. The length of Period T2 is significantly different depending on the photographing methods and conditions and the like, and is about 1 millisecond to about several hundreds of milliseconds, for example.

When the integrated value of the signals read out from the detection pixels 121 arranged in the radiation detection region (ROI) has reached the dose A1, the control unit 225 causes the operation of the radiation imaging apparatus 200 to transition to Period T3. At this time, the control unit 225 also outputs the exposure stop signal to the radiation source interface 1004 via the communication interface 1003. Then, the radiation source 1005 stops the radiation irradiation.

Period T3 is a period during which, after the radiation source 1005 terminates the radiation irradiation, radiation image signals are read out from the imaging pixels 101 and the detection pixels 121. In Period T3, a plurality of rows are scanned to sequentially set the signals Vg1 to Vgn to the high level, and to sequentially set the signals Vd1 to Vdn to the high level at the same timings as the signals Vg1 to Vgn. The first switches 103, the second switches 123, and the third switches 126 in each row sequentially enter the conductive state. In the imaging pixel 101, the first switch 103 enters the conductive state, and the voltage corresponding to the amount of charge stored in the first conversion element 102 is output to the column signal line 106. The signals Vd1 to Vdn are set to the high level at the same timings as the signals Vg1 to Vgn so that in the detection pixel 121, the second switch 123 and the third switch 126 enter the conductive state. As a result, voltages corresponding to amounts of charge stored in both of the second conversion element 122 and the storage capacitor 127 are output to the column signal lines 106. The readout unit 130 reads out the signals from the column signal lines 106. The signal processing unit 224 monitors an amount of radiation based on an output signal of the AD converter 136. As a result, an amount of image signals is not attenuated, and also in the detection pixels 121, all the signals stored in the second conversion element 122 and the storage capacitor 127 may be used as pixel signals (image signals).

As opposed to the above-mentioned operation, in a case where only the signals Vg1 to Vgn are set to the high level, the amounts of charge stored in the second conversion elements 122 may be read out, but the amounts of charge stored in the storage capacitors 127 cannot be read out. In order to correctly read out image signals, there is a need to set the signals Vd1 to Vdn to the high level at the same timings as the signals Vg1 to Vgn. The signals stored in the imaging pixels 101 and the detection pixels 121 are read out by the readout unit 130. In this example, in order to uniformize storage times in respective imaging pixels 101, depending on the signal Vg1 of the last row to which the high level has been applied in Period T1, the signal Vg2 of the first row to apply the high level is determined in Period T3. In FIG. 6, the last row to which the high level has been applied in Period T1 is the row corresponding to the signal Vg1, and hence the high level is applied in order from the row corresponding to the signal Vg2 in Period T3.

Moreover, in this embodiment, the second switches 123 of the detection pixels 121 are provided so that the radiation irradiation may be detected for each detection pixel 121 while reducing the number of detection signal lines 125. Therefore, the layout is not restricted, and a radiation irradiation amount in an arbitrary detection region may be monitored at an arbitrary timing. Here, the configuration in which the radiation may be detected for each detection pixel 121, or for each radiation detection region (ROI) including at least one detection pixel 121 contributes to realization of more appropriate dose control and exposure control.

Figure 7:
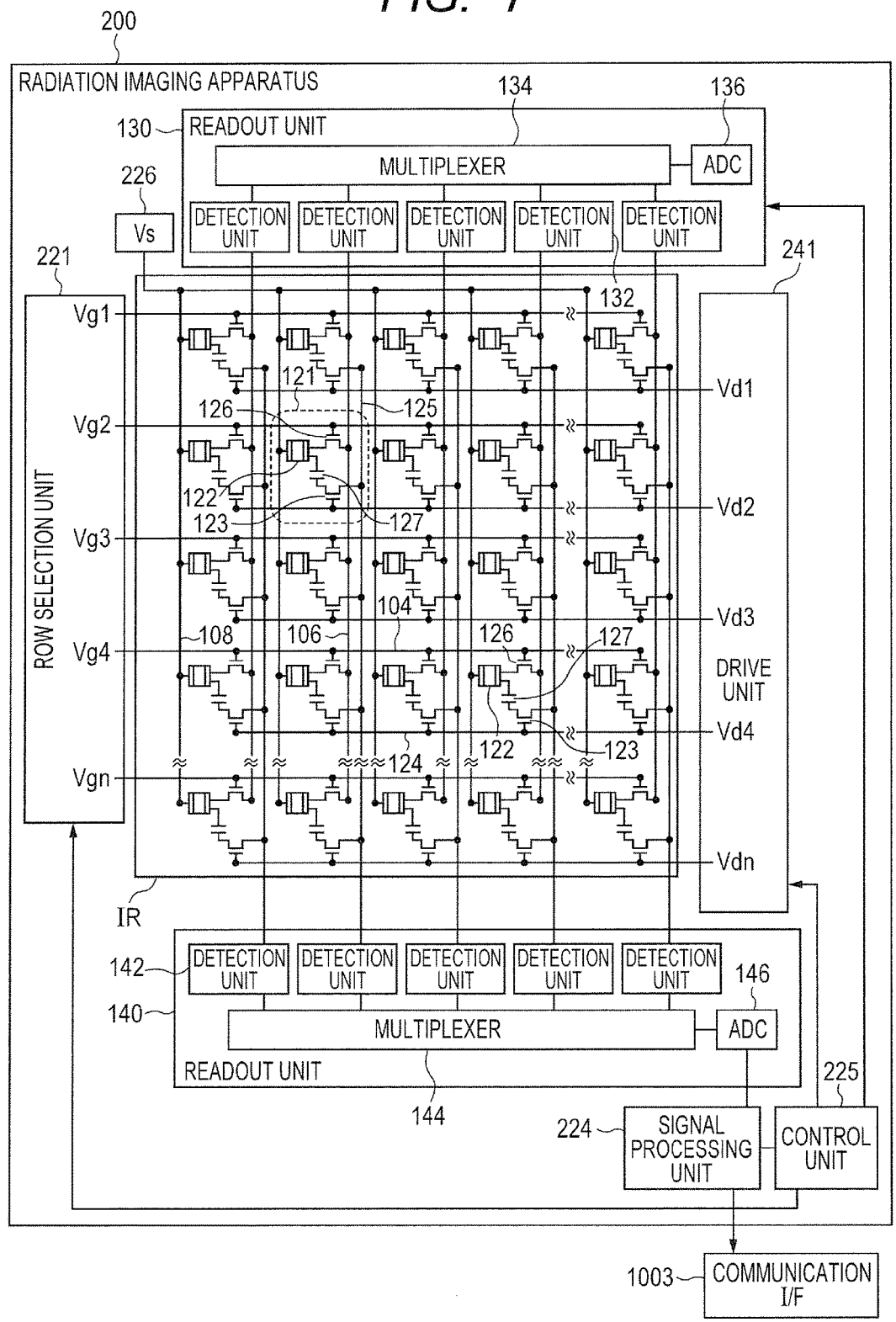
FIG. 7 is a diagram for illustrating another configuration example of the radiation imaging apparatus.

Moreover, in this embodiment, also in the detection pixels 121 configured to monitor the radiation, the pixel signals (image signals) may be obtained. Every one (each) of the plurality of pixels in matrix may be formed of the detection pixel 121 as in FIG. 7. When such a configuration as in FIG. 7 is adopted, the radiation detection region (ROI) may be set in units of a pixel in any part of the imaging region IR.

Figure 8:
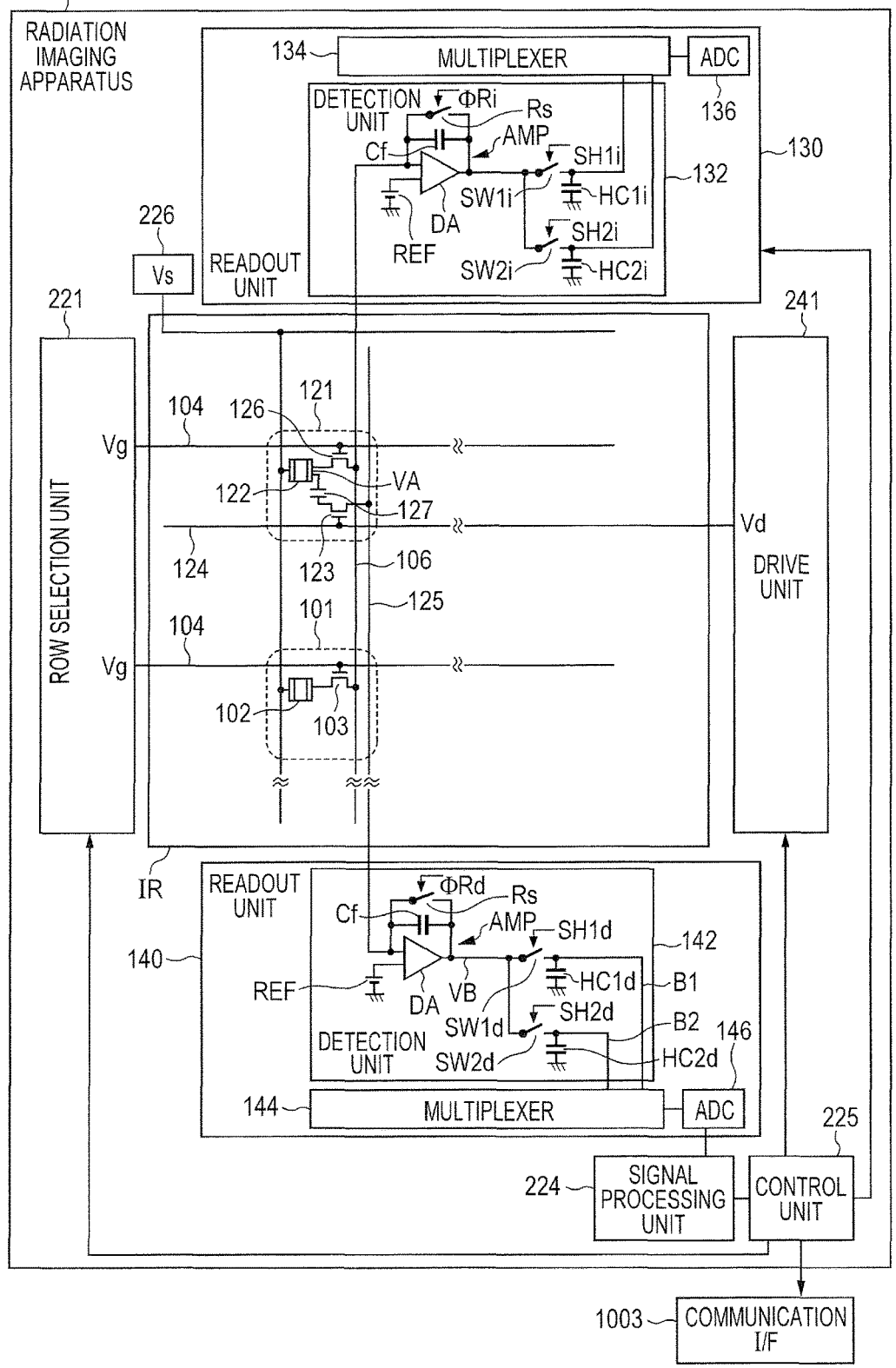
FIG. 8 is a diagram for illustrating a configuration example of the radiation imaging apparatus.

In FIG. 8, a configuration example of the readout unit 130 and the readout unit 140 is illustrated. The detection unit 132 of the readout unit 130 includes an amplifier circuit AMP, a first holding capacitor HC1$i$, a second holding capacitor HC2$i$, a first sampling switch SW1$i$, and a second sampling switch SW2$i$. The amplifier circuit AMP includes an amplifier DA having a first input terminal, a second input terminal, and an output terminal, and a feedback capacitor Cf and a reset switch RS, which are provided in parallel between the above-mentioned first input terminal and the above-mentioned output terminal. The reset switch RS enters a conductive state or a non-conductive state depending on a reset signal ΦRi. To the above-mentioned first input terminal, the column signal line 106 is connected. To the above-mentioned second terminal, a reference potential REF is supplied. The first sampling switch SW1$i$ is connected between the output terminal of the amplifier DA (amplifier circuit AMP) and the first holding capacitor HC1$i$. The first sampling switch SW1$i$ connects the output terminal of the amplifier DA (amplifier circuit AMP) and the first holding capacitor HC1$i$ in response to a sampling signal SH1$i$. The second sampling switch SW2$i$ connects the output terminal of the amplifier DA (amplifier circuit AMP) and the second holding capacitor HC2$i$ in response to a sampling signal SH2$i$.

The detection unit 142 of the readout unit 140 includes an amplifier circuit AMP, a first holding capacitor HC1$d$, a second holding capacitor HC2$d$, a first sampling switch SW1$d$, and a second sampling switch SW2$d$. The amplifier circuit AMP includes an amplifier DA having a first input terminal, a second input terminal, and an output terminal, and a feedback capacitor Cf and a reset switch RS, which are provided in parallel between the above-mentioned first input terminal and the above-mentioned output terminal. The reset switch RS enters the conductive state or the non-conductive state depending on a reset signal ΦRd. To the above-mentioned first input terminal, the detection signal line 125 is connected. To the above-mentioned second terminal, the reference potential REF is supplied. The first sampling switch SW1$d$ connects the output terminal of the amplifier DA (amplifier circuit AMP) and the first holding capacitor HC1$d$ in response to a sampling signal SH1$d$. The second sampling switch SW2$d$ connects the output terminal of the amplifier DA (amplifier circuit AMP) and the second holding capacitor HC2$d$ in response to a sampling signal SH2$d$. A potential VA is a potential of the first electrode 131 (FIG. 5A) of the detection pixel 121, and a potential VB is a potential of the output terminal of the amplifier DA (amplifier circuit AMP) in the detection unit 142.

Figure 9:
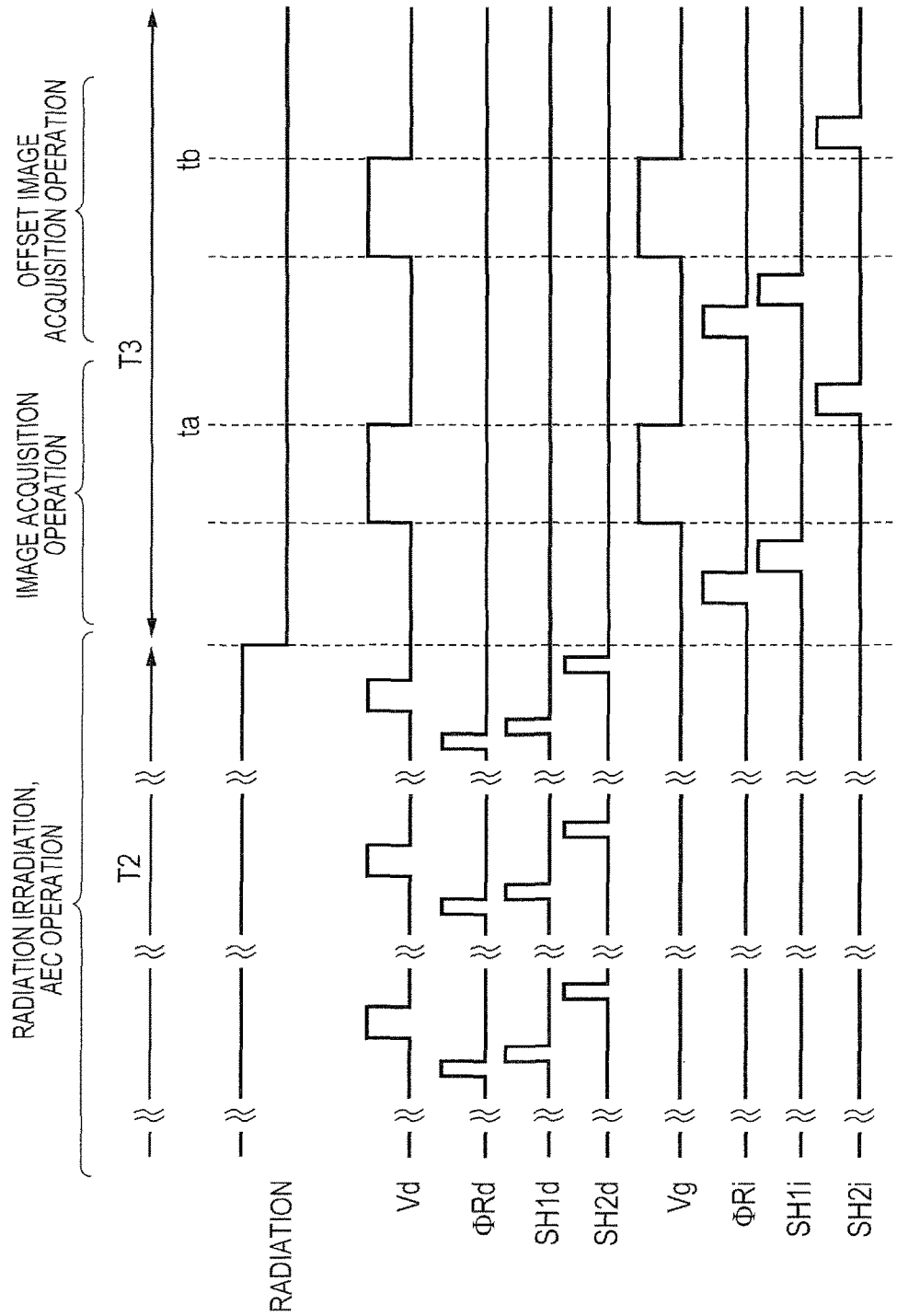
FIG. 9 is a timing chart for illustrating operations of the radiation imaging apparatus.

FIG. 9 is a timing chart for illustrating an example of operations of the readout unit 130 and the readout unit 140 of FIG. 8. A signal Vd corresponds to the signals Vd1 to Vdn in FIG. 6, and a signal Vg corresponds to the signals Vg1 to Vgn in FIG. 6. In FIG. 9, Period T2 and Period T3 in FIG. 6 are shown. First, in Period T2, in the readout unit 140, the reset signal ΦRd is set to the high level so that the reset switch RS enters the conductive state. As a result, the potential VB is reset to the reference potential REF.

Next, the sampling signal SH1$d$ changes from the low level to the high level, and then from the high level to the low level to turn on the first sampling switch SW1$d$ and sample an output signal of the amplifier DA in the first holding capacitor HC1$d$. A signal B1 of the first holding capacitor HC1$d$ is output to the signal processing unit 224 via the multiplexer 144 and the AD converter 146.

Next, the signal Vd applied to the drive line 124 changes to the high level so that the second switch 123 of the detection pixel 121 enters the conductive state. At this time, the signal corresponding to the amount of charge stored in the storage capacitor 127 is transmitted to the readout unit 140 via the detection signal line 125.

Next, in the readout unit 140, the sampling signal SH2$d$ changes from the low level to the high level, and then from the high level to the low level to turn on the second sampling switch SW2$d$ and sample the output signal of the amplifier DA in the second holding capacitor HC2$d$. A signal B2 of the second holding capacitor HC2$d$ is output to the signal processing unit 224 via the multiplexer 144 and the AD converter 146.

Next, the signal processing unit 224 may compute a difference between the signal B2 and the signal B1 to detect a net radiation component (irradiation amount of the radiation). Note that, in the above-mentioned example, the example in which the signal processing unit 224 computes the difference between the signal B1 and the signal B2 has been described, but a differential circuit may be arranged in the readout unit 140 so that the differential circuit in the readout unit 140 outputs a signal of the difference between the signal B1 and the signal B2.

The above-mentioned operations are repeated to monitor the amount of radiation, and when the integrated value of the signals read out from the detection pixels 121 arranged in the radiation detection region (ROI) has reached the dose A1, the control unit 225 causes the operation of the radiation imaging apparatus 200 to transition to Period T3. At this time, the control unit 225 also outputs the exposure stop signal to the radiation source interface 1004 via the communication interface 1003 (FIG. 2). Then, the radiation source 1005 stops the radiation irradiation. After the radiation irradiation is terminated, the operation transitions to Period T3, and in an image acquisition operation, the radiation image signals are read out from the imaging pixels 101 and the detection pixels 121.

In Period T3, first, in the readout unit 130, the reset signal ΦRi is set to the high level so that the reset switch RS enters the conductive state, and an output potential of the amplifier DA is reset to the reference potential REF. Next, the sampling signal SH1$i$ changes from the low level to the high level, and then from the high level to the low level to turn on the first sampling switch SW1$i$ and sample the output signal of the amplifier DA in the first holding capacitor HC1$i$.

Next, the signal Vg applied to the drive line 104 and the signal Vd applied to the drive line 124 are set to the high level so that the second switch 123 and the third switch 126 of the detection pixel 121 enter the conductive state, and so that the first switch 103 of the imaging pixel 101 enters the conductive state. In the detection pixel 121, the signals corresponding to the amounts of charge stored in the second conversion element 122 and the storage capacitor 127 are output to the readout unit 130 via the column signal line 106. In the imaging pixel 101, the signal corresponding to an amount of charge stored in the first conversion element 102 is output to the readout unit 130 via the column signal line 106.

Next, the sampling signal SH2$i$ changes from the low level to the high level, and then from the high level to the low level to turn on the second sampling switch SW2$i$ and sample the output signal of the amplifier DA in the second holding capacitor HC2$i$. The signal processing unit 224 may output a difference between the signal stored in the second holding capacitor HC2$i$ and the signal stored in the first holding capacitor HC1$i$ to detect the net radiation component (irradiation amount of the radiation). Thereafter, in an offset image acquisition operation, processing similar to the above-mentioned image acquisition operation is performed.

As described above, in Period T2, the readout unit 140 resets a potential of the detection signal line 125 with the reset signal ΦRd. Thereafter, the readout unit 140 reads out a first signal from the detection signal line 125 in the non-conductive state of the second switch 123 with the sampling signal SH1$d$. Thereafter, the readout unit 140 reads out a second signal from the detection signal line 125 in the conductive state of the second switch 123 with the sampling signal SH2$d$. The signal processing unit 224 computes a difference between a signal based on the above-mentioned first signal and a signal based on the above-mentioned second signal.

In the configuration in FIG. 8, an example in which, in Period T3 during which the radiation image signals are read out, the signal Vd applied to the drive line 124 is controlled at the same timing as the signal Vg applied to the drive line 104 has been described, but this embodiment is not limited thereto. At least in Period T3, at time points ta and tb at which the signal Vg applied to the drive line 104 transitions from the high level to the low level, the signal Vd applied to the drive line 124 only needs to be at the high level for a period during which the charge in the storage capacitor 127 is sufficiently discharged. Therefore, as long as this condition is satisfied, the operation may be performed so that the period during which the signal Vd applied to the drive line 124 is maintained at the high level is shorter than that of the signal Vg applied to the drive line 104. In other words, in a state in which at least a part of a conduction period of the second switch 123 overlaps a conduction period of the third switch 126, the readout unit 130 reads out the signals from the column signal lines 106. Alternatively, as in FIG. 10, the signal Vd may be maintained at the high level from before the reset signal ΦRi is set to the high level to after the sampling is performed in the second holding capacitor HC2$i$. In this case, while the signal Vd is maintained at the high level, a high-level pulse of the signal Vg is generated.

Second Embodiment

As compared to the radiation imaging apparatus 200 according to the first embodiment, a radiation imaging apparatus 200 according to a second embodiment of the present invention is the same in terms of the configuration (FIG. 8), and is different in terms of the operational method. The second embodiment is different from the first embodiment in terms of the driving method at the time of detecting the radiation, and is intended to take measures against crosstalk. Now, differences of this embodiment from the first embodiment are described.

Figure 10:
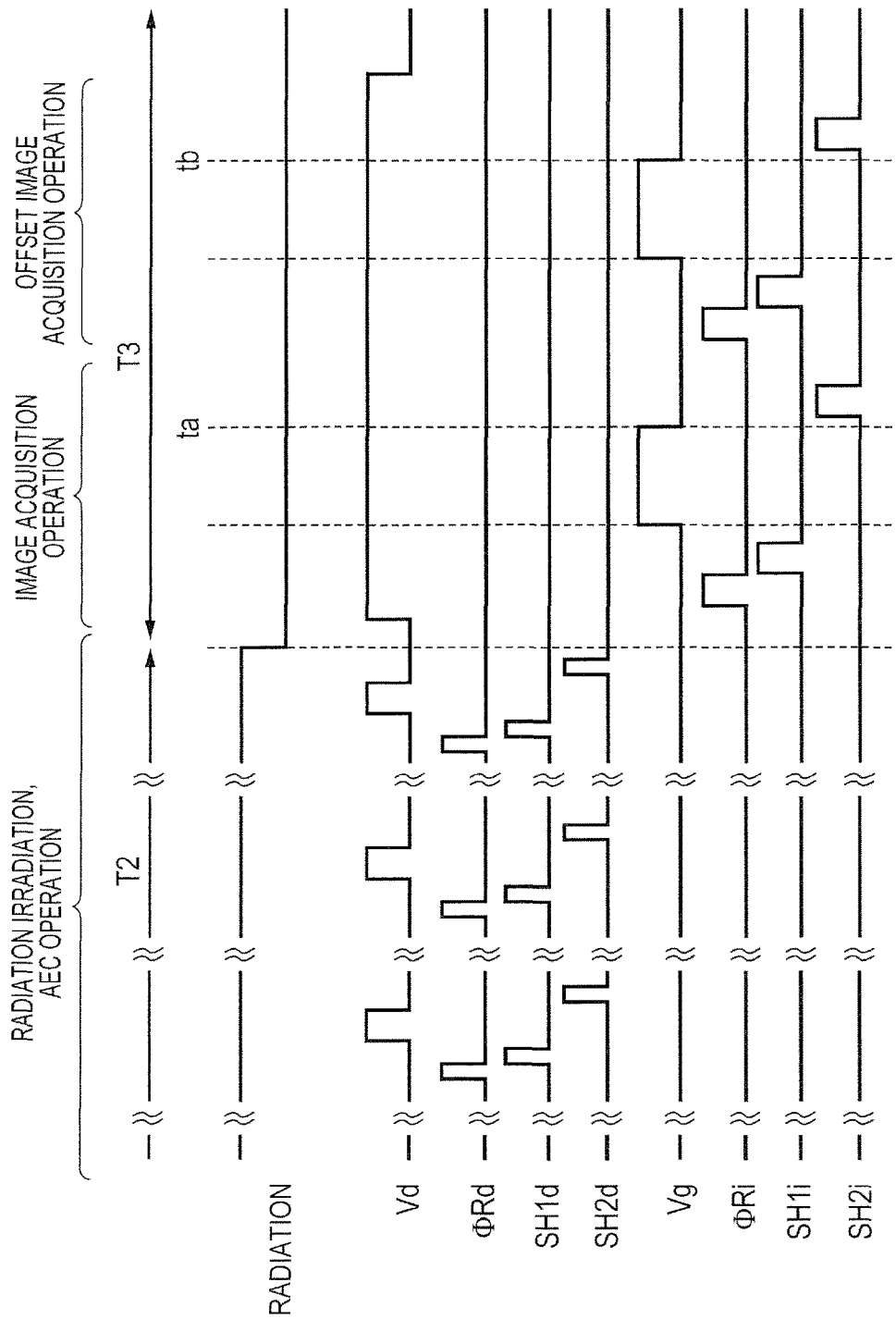
FIG. 10 is a timing chart for illustrating operations of the radiation imaging apparatus.
Figure 11:
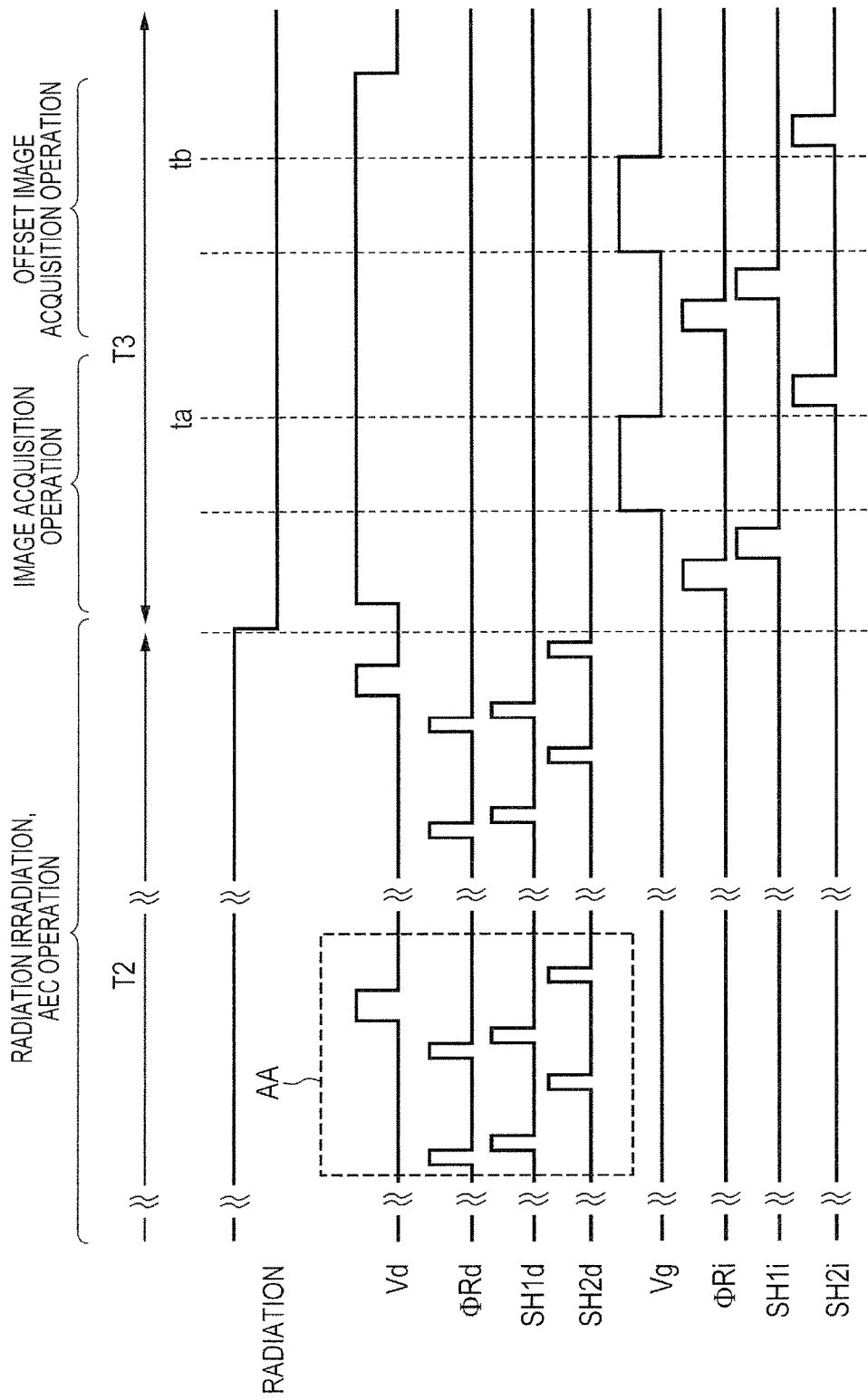
FIG. 11 is a timing chart for illustrating operations of the radiation imaging apparatus.
Figure 12:
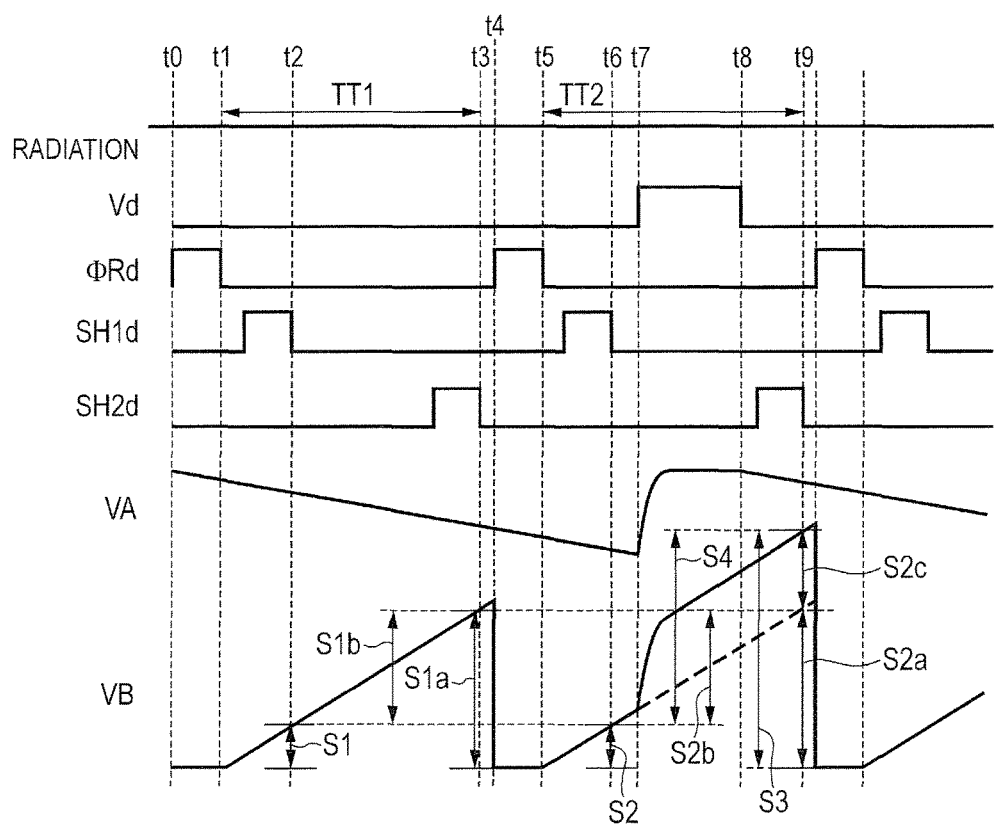
FIG. 12 is a timing chart for illustrating operations of the radiation imaging apparatus.

FIG. 11 is a timing chart for illustrating an example of operations of the readout units 130 and 140 of FIG. 8, and FIG. 12 is a detailed timing chart of the area AA in FIG. 11. As illustrated in FIG. 8, the potential VA is the potential of the first electrode 131 (FIG. 5A) of the detection pixel 121, and the potential VB is the potential of the output terminal of the amplifier DA (amplifier circuit AMP) in the detection unit 142. Now, differences of FIG. 11 from FIG. 10 are described.

Period T2 is a period during the radiation irradiation. In Period T2, the potential VA of the first electrode 131 of the detection pixel 121 varies. With the variation, the potential of the detection signal line 125 is changed due to the crosstalk via parasitic capacitance between the second electrode 137 and the detection signal line 125. Therefore, as exemplified in FIG. 12, the potential VB of the output terminal of the amplifier DA (amplifier circuit AMP) also varies. Crosstalk components (CT components) S1, S1$a$, S2, and S2$a$ of the potential VB indicate changes in potential VB corresponding to changes in potential of the detection signal line 125 due to the crosstalk. Moreover, a radiation component S2$c$ of the potential VB indicates a change in potential VB corresponding to a change in potential of the detection signal line 125 caused by the conduction of the second switch 123 (that is, the charge stored in the second conversion element 122). A signal (crosstalk component) S2 is a signal stored in the first holding capacitor HC1$d$ when the sampling signal SH1$d$ is set to the high level so that the first sampling switch SW1$d$ enters the conductive state. A signal S3 is a signal stored in the second holding capacitor HC2$d$ when the sampling signal SH2$d$ is set to the high level so that the second sampling switch SW2$d$ enters the conductive state. The signal S2 is a crosstalk component. The signal S3 has the crosstalk component S2$a$ and the radiation component S2$c$. The signal processing unit 224 outputs a differential signal S4 between the signal S2 and the signal S3. The crosstalk component S2$a$ of the signal S3 is different from the signal (crosstalk component) S2, and hence the differential signal S4 between the signal S2 and the signal S3 contains the crosstalk component S2$a$ and the radiation component S2$c$. Therefore, the radiation component S2$c$ cannot be obtained correctly in some cases even when the signal processing unit 224 outputs the differential signal S4 between the signal S2 and the signal S3.

Next referring to FIG. 12, an operation for reducing the effect of the crosstalk is described. First, at Time t0, in the detection pixel 121, the reset signal ΦRd is set to the high level so that the reset switch RS enters the conductive state. As a result, the potential VB is reset to the reference potential REF. At Time t1, in the detection pixel 121, the reset signal ΦRd is set to the low level so that the reset switch RS enters the non-conductive state, and the potential VB starts to change due to the crosstalk of the potential VA.

Next, the sampling signal SH1$d$ changes from the low level to the high level, and at the following Time t2, the sampling signal SH1$d$ changes from the high level to the low level. The first sampling switch SW1$d$ enters the conductive state, and the output signal of the amplifier DA is sampled in the first holding capacitor HC1$d$. As a result, the signal S1 corresponding to a crosstalk component at Time t2 is held in the first holding capacitor HC1$d$. The signal S1 is output to the signal processing unit 224 via the multiplexer 144 and the AD converter 146.

Next, the sampling signal SH2$d$ changes from the low level to the high level, and at the following Time t3, the sampling signal SH2$d$ changes from the high level to the low level. The second sampling switch SW2$d$ enters the conductive state, and the output signal of the amplifier DA is sampled in the second holding capacitor HC2$d$. As a result, a signal S1$a$ corresponding to a crosstalk component at Time t3 is held in the second holding capacitor HC1$d$. The signal S1a is output to the signal processing unit 224 via the multiplexer 144 and the AD converter 146.

Next, the signal processing unit 224 outputs a differential signal S1b between the signal S1 and the signal S1a. The differential signal S1b corresponds to a crosstalk component in Period TT1 from Time t1 to Time t3. Note that, the differential signal S1b is a difference between two sampling results after the reset signal ΦRd has caused the reset switch RS to enter the non-conductive state, and hence KTC noise has been removed.

Next, at Time t4, in the detection pixel 121, the reset signal ΦRd is set to the high level so that the reset switch RS enters the conductive state. As a result, the potential VB is reset to the reference potential REF. Next, at Time t5, in the detection pixel 121, the reset signal ΦRd is set to the low level so that the reset switch RS enters the non-conductive state, and the potential VB starts to change due to the crosstalk of the potential VA.

Next, the sampling signal SH1d changes from the low level to the high level, and at the following Time t6, the sampling signal SH1d changes from the high level to the low level. The first sampling switch SW1d enters the conductive state, and the output signal of the amplifier DA is sampled in the first holding capacitor HC1d. As a result, the signal S2 corresponding to a crosstalk component at Time t6 is held in the first holding capacitor HC1d. The signal S2 is output to the signal processing unit 224 via the multiplexer 144 and the AD converter 146.

Next, in a period from Time t7 to Time t8, a potential Vd of the drive line 124 is set to the high level so that the second switch 123 enters the conductive state. At this time, the potential VB changes depending on the amount of charge stored in the second conversion element 122. Moreover, even in a state in which the second switch 123 is in the conductive state, the radiation continues to be irradiated, and hence the potential VB continues to change due to the crosstalk of the potential VA.

Next, the sampling signal SH2d changes from the low level to the high level, and at the following Time t9, the sampling signal SH2d changes from the high level to the low level. The second sampling switch SW2d enters the conductive state, and the output signal of the amplifier DA is sampled in the second holding capacitor HC2d. As a result, the signal S3 is held in the second holding capacitor HC2d. The signal S3 contains the crosstalk component S2a and the radiation component S2c, and is output to the signal processing unit 224 via the multiplexer 144 and the AD converter 146.

Next, the signal processing unit 224 outputs the differential signal S4 between the signal S2 and the signal S3. The differential signal S4 contains not only the radiation component S2c but also the crosstalk component S2a in Period TT2. Note that, the differential signal S4 is a difference between two sampling results after the reset signal ΦRd has caused the reset switch RS to enter the non-conductive state, and hence KTC noise has been removed. Moreover, in the above-mentioned example, the example in which the signal processing unit 224 computes the difference between the signals has been described, but a differential circuit may be arranged in the readout unit 140 so that the differential circuit in the readout unit 140 computes the difference between the signals.

Here, the crosstalk component S2 is substantially the same as the crosstalk component S1. The crosstalk component S2a is substantially the same as the crosstalk component S1a. Therefore, a differential signal S2b between the crosstalk components S2 and S2a is substantially the same as the differential signal S1b between the crosstalk components S1 and S1a. Therefore, the signal processing unit 224 may compute a difference between the differential signal S4 and the differential signal S1b to output a net radiation component (irradiation amount of the radiation) S2c and reduce the crosstalk components. Note that, the differential signal S1b and the differential signal S4 do not contain the KTC noise, and hence the difference between the differential signal S4 and the differential signal S1b does not contain the KTC noise, either. Here, Period TT1 and Period TT2 may be set equal to make the crosstalk component S1a and the crosstalk component S2a substantially the same.

Here, the differential signal S1b is an amount of change in signal appearing on the detection signal line 125 in a state in which the second switch 123 is non-conductive after the potential of the detection signal line 125 is reset to the reference potential REF. The differential signal S2b is an amount of change in signal appearing on the detection signal line 125 when the second switch 123 is changed from the non-conductive state to the conductive state after the potential of the detection signal line 125 is reset to the reference potential REF.

As described above, at Time t0 and Time t1, the readout unit 140 resets the potential of the detection signal line 125 with the reset signal ΦRd. Thereafter, at Time t2, the readout unit 140 reads out the signal S1 based on the first signal from the detection signal line 125 in the non-conductive state of the second switch 123 with the sampling signal SH1d. Thereafter, at Time t3, the readout unit 140 reads out the signal S1a based on the second signal from the detection signal line 125 in the non-conductive state of the second switch 123 with the sampling signal SH2d. Thereafter, at Time t4 and Time t5, the readout unit 140 resets the potential of the detection signal line 125 with the reset signal ΦRd. Thereafter, at Time t6, the readout unit 140 reads out the signal S2 based on a third signal from the detection signal line 125 in the non-conductive state of the second switch 123 with the sampling signal SH1d. Thereafter, at Time t9, the readout unit 140 reads out the signal S3 based on a fourth signal from the detection signal line 125 in the conductive state of the second switch 123 with the sampling signal SH2d.

The signal processing unit 224 computes a difference between the signal S1 based on the first signal and the signal S1a based on the second signal as a fifth signal S1b, and a difference between the signal S2 based on the third signal and the signal S3 based on the fourth signal as a sixth signal S4. Then, the signal processing unit 224 computes a difference between the fifth signal S1b and the sixth signal S4 to obtain the radiation component S2c.

The signal processing unit 224 may compute the difference between the sixth signal S4 and the fifth signal S1b to remove a crosstalk component S2b and detect the radiation component S2c with high accuracy. In particular, in the detection of the start of the radiation irradiation, the detection of the integrated irradiation amount (dose) of the radiation, and the like, the signals need to be read out in a short period of time, and hence a signal value is small. Therefore, the significance of removing the crosstalk component S2b is great.

Third Embodiment

Figure 13:
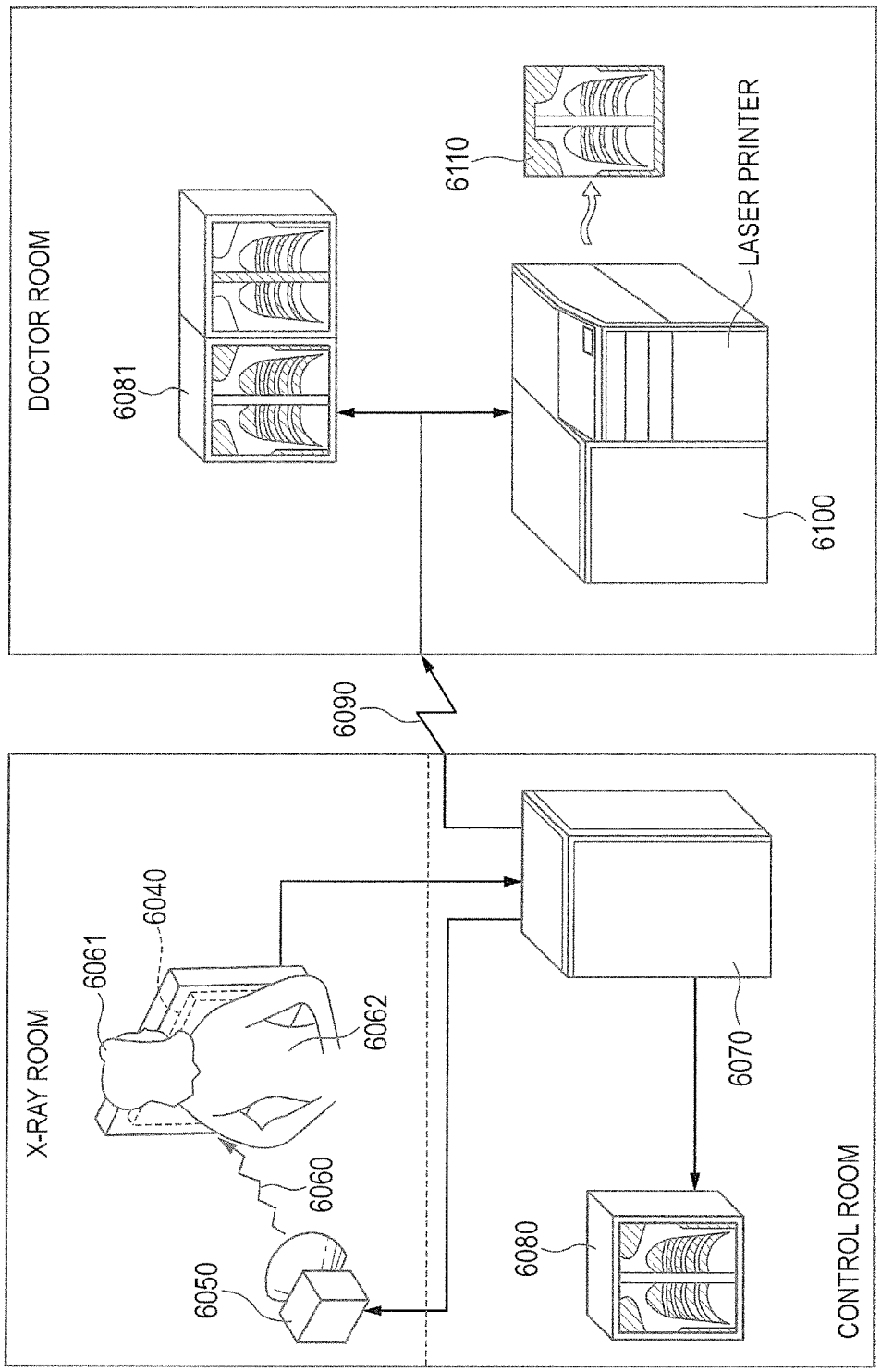
FIG. 13 is a diagram for illustrating a configuration example of a radiation imaging system.

In FIG. 13, a configuration example of a radiation imaging system according to a third embodiment of the present invention is illustrated. The radiation imaging system includes a radiation imaging apparatus 6040. The radiation imaging apparatus 6040 corresponds to the radiation imaging apparatus 200 in the first or second embodiment. An X-ray 6060 generated by an X-ray tube 6050, which is the radiation source, is transmitted through a chest 6062 of a patient or subject 6061, and enters the radiation imaging apparatus 6040 represented by the above-mentioned radiation imaging apparatus 200. The incident X-ray contains information inside the body of the subject 6061. The scintillator emits light to correspond to the incident X-ray, and the light is photoelectrically converted by the photoelectric conversion element to obtain electrical information. This information is digitally converted, and subjected to image processing by an image processor 6070 serving as a signal processing unit so that the information may be observed on a display 6080 serving as a display unit in a control room.

Moreover, the information may be transferred to a remote site by a transmission processing unit such as a telephone line 6090 so that the information may be displayed on a display 6081 serving as a display unit in a doctor room or the like at a different place or saved on a recording unit such as an optical disc and may be diagnosed by a doctor at the remote site. Moreover, the information may be recorded on a film 6110 serving as a recording medium by a film processor 6100 serving as the recording unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-058128, filed Mar. 20, 2015, which is hereby incorporated by reference herein in its entirety.

The invention claimed is:

1. A radiation imaging apparatus, comprising:
    a plurality of pixels configured to output image signals corresponding to radiation;
    an image signal line configured to output the image signals; and
    a detection signal line configured to output a detection signal for detection of irradiation of the radiation,
    wherein at least one of the plurality of pixels comprises:
        a conversion element configured to convert the radiation into charge;
        a first switch configured to output the image signal corresponding to the charge via the image signal line;
        a storage capacitor including a first electrode and a second electrode, in which the first electrode is electrically connected to the conversion element to store the charge; and
        a second switch configured to electrically connect the second electrode and the detection signal line.

2. A radiation imaging apparatus according to claim 1, wherein another pixel different from the at least one of the plurality of pixels includes the conversion element and the first switch.

3. A radiation imaging apparatus according to claim 1, wherein the plurality of pixels are arranged in matrix, and the detection signal line is provided separately from the image signal line,
    wherein the first switches of pixels arranged in one column of the plurality of pixels are electrically connected in common to the image signal line, and
    wherein the second switches of the pixels arranged in the one column are electrically connected in common to the detection signal line.

4. A radiation imaging apparatus according to claim 3, further comprising:
    a first readout unit configured to read out signals from the detection signal line; and
    a second readout unit configured to read out signals from the image signal line.

5. A radiation imaging apparatus according to claim 4, further comprising:
    a first drive line connected in common to the first switches of pixels arranged in one row of the plurality of pixels;
    a second drive line connected in common to the second switches of the pixels arranged in the one row;
    a first drive unit electrically connected to the first drive line; and
    a second drive unit electrically connected to the second drive line.

6. A radiation imaging apparatus according to claim 5, further comprising a control unit configured to control the first drive unit, the second drive unit, the first readout unit, and the second readout unit.

7. A radiation imaging apparatus according to claim 6, wherein the control unit is configured to control the first drive unit, the second drive unit, and the second readout unit so that the second readout unit reads out the signals from the image signal line in a state in which at least a part of a conduction period of the second switch overlaps a conduction period of the first switch.

8. A radiation imaging apparatus according to claim 6, wherein the control unit is configured to control the second drive unit and the first readout unit so that the first readout unit resets a potential of the detection signal line, then reads out a first signal from the detection signal line in a non-conductive state of the second switch, and then reads out a second signal from the detection signal line in a conductive state of the second switch.

9. A radiation imaging apparatus according to claim 8, further comprising a signal processing unit configured to compute a difference between a signal based on the first signal and a signal based on the second signal.

10. A radiation imaging apparatus according to claim 6, wherein the control unit is configured to control the second drive unit and the first readout unit so that the first readout unit resets a potential of the detection signal line, then reads out a first signal from the detection signal line in a non-conductive state of the second switch, then reads out a second signal from the detection signal line in the non-conductive state of the second switch, then resets the potential of the detection signal line, then reads out a third signal from the detection signal line in the non-conductive state of the second switch, and then reads out a fourth signal from the detection signal line in the conductive state of the second switch.

11. A radiation imaging apparatus according to claim 10, further comprising a signal processing unit configured to compute a difference between a signal based on the first signal and a signal based on the second signal as a fifth signal, compute a difference between a signal based on the third signal and a signal based on the fourth signal as a sixth signal, and compute a difference between the fifth signal and the sixth signal.

12. A radiation imaging system, comprising:
    the radiation imaging apparatus of claim 1; and
    a radiation source configured to irradiate radiation.

* * * * *